(12) United States Patent
Kang et al.

(10) Patent No.: US 8,530,205 B2
(45) Date of Patent: Sep. 10, 2013

(54) BUFFER COMPOSITION FOR CATALYZING THE PREPARATION OF CALCITRIOL OR CALCIFEDIOL AND METHOD FOR PREPARING CALCITRIOL OR CALCIFEDIOL USING SAME

(75) Inventors: Dae-Jung Kang, Yongin-si (KR); Jong-Hyuk Im, Gwacheon-si (KR); Hyun-Jung Jung, Hwaseong-si (KR); Jae-Hoon Kang, Seoul (KR)

(73) Assignee: IL Dong Pharm Co., Ltd., Seoul (KR)

( * ) Notice: Subject to any disclaimer, the term of this patent is extended or adjusted under 35 U.S.C. 154(b) by 0 days.

(21) Appl. No.: 13/162,246

(22) Filed: Jun. 16, 2011

(65) Prior Publication Data

US 2012/0064584 A1  Mar. 15, 2012

Related U.S. Application Data

(63) Continuation of application No. PCT/KR2009/007404, filed on Dec. 10, 2009.

(30) Foreign Application Priority Data

Dec. 19, 2008 (KR) .......................... 10-2008-0130707

(51) Int. Cl.
*C12P 15/00* (2006.01)
*C12N 9/52* (2006.01)

(52) U.S. Cl.
USPC ........................................ 435/127; 435/220

(58) Field of Classification Search
None
See application file for complete search history.

(56) References Cited

FOREIGN PATENT DOCUMENTS

EP  2 130 916 A1 *  9/2009
KR  10-0861181 B1   9/2008

OTHER PUBLICATIONS

Fujii et al., Purification, characterization, and directed evolution study of a vitamin D3 hydroxylase from *Pseudonocardia autotrophica*, Biochemical and Biophysical Research Communications, 385 (2009) 170-175.*
http://liveweb.archive.org/http://bccm.belspo.be/db/media_search_results.php?COLL=LMG&TEXT1=trace (last downloaded Oct. 18, 2012.*
Kang et al., Biotechnol. Bioprocess Eng., vol. 11, pp. 408-413 (2006).
Sasaki, J. et al., Appl. Microbiol. Biotechnol., vol. 38, pp. 152-157 (1992).
Takeda, K. et al., J. Ferment. Bioeng., vol. 78, No. 5, pp. 380-382 (1994).
Takeda. K. et al., Steriods, vol. 71, pp. 736-744 (2006).
PCT International Search Report dated Jul. 30, 2010, from corresponding PCT patent application No. PCT/KR2009/007404.
PCT International Preliminary Report on Patentability from corresponding PCT patent application No. PCT/KR2009/007404.

* cited by examiner

*Primary Examiner* — Suzanne M Noakes
*Assistant Examiner* — Stephen Chong
(74) *Attorney, Agent, or Firm* — Edwards Wildman Palmer LLP

(57) ABSTRACT

The present invention relates to a buffer composition for promoting production of calcitriol or calcifediol, and a method for producing calcitriol or calcifediol using the same. More particularly, the present invention relates to a buffer composition for promoting production of calcitriol or calcifediol comprising a metallic compound, an organic solvent, cyclodextrin, tris(hydroxymethyl)aminomethane, sodium succinate, sodium chloride, magnesium chloride, and water, and a method for producing calcitriol or calcifediol using the same. In the method for producing calcitiriol or calcifediol, the production yield of calcitriol or calcifediol is high, and the bioconversion is carried out in an enzyme reaction system instead of in a microorganism culture system. Thus, it is not required to maintain a sterile state. Also, the separation/purification following the completion of a biocatalytic reaction can be carried out in a cleaner state than the microorganism culture method. Accordingly, there is an advantage in that a cost required for separation is low and the quality is improved. Furthermore, the buffer composition for promoting production of calcitriol or calcifediol can provide a high productivity of calcitriol or calcifediol.

7 Claims, 9 Drawing Sheets

Biotransformation

Chemical synthesis

BUFFER COMPOSITION FOR CATALYZING THE PREPARATION OF CALCITRIOL OR CALCIFEDIOL AND METHOD FOR PREPARING CALCITRIOL OR CALCIFEDIOL USING SAME

CROSS-REFERENCE TO RELATED APPLICATIONS

This application is a continuation of PCT/KR2009/007404 filed on Dec. 10, 2009, which claims priority to Korean Application No. 10-2008-0130707 filed on Dec. 19, 2008, the entire contents of which applications are incorporated herein by reference.

TECHNICAL FIELD

The present invention relates to a buffer composition promoting calcitriol or calcifediol production, and a method for producing calcitriol or calcifediol using the same. More particularly, the present invention relates to a buffer composition promoting calcitriol or calcifediol production including a metallic compound, an organic solvent, cyclodextrin, tris(hydroxymethyl)aminomethane, sodium succinate, sodium chloride, magnesium chloride, and water, and a method for producing calcitriol or calcifediol using the same.

BACKGROUND ART

Calcitriol is widely used for treating osteoporosis which is a representative disease affecting the elderly, and calcifediol which is activated vitamin D3, is used for treating osteomalacia, etc. Calcitriol, which is generated by two respective hydroxylations of vitamin D3 in the liver and kidney, is a biogenic material, and can be simply administered orally. Also, it is known that calcitriol physiologically promotes the absorption of calcium and phosphorus in gastrointestinal organs and the kidney, and thus shows a high therapeutic effect on osteoporosis.

Also, calcitriol is used for treating rickets, osteomalacia, hypoparathyroidism, chronic renal failure, hemodialysis patient's renal osteodystrophy, and psoriasis, and its therapeutic effect on prostate cancer or myelogenous leukemia has been recently reported well.

As a method for preparing calcitriol or calcifediol, a preparation method by organic chemical synthesis and microorganism fermentation has been conventionally known. The organic chemical synthesis has a disadvantage in that it requires a highly complicated technology and an expensive reaction process because a hydroxyl group has to be selectively introduced into a 1- or 25-position of a carbon chain in consideration of stereospecificity and regiospecificity in a chemical structure. Then, in order to solve this disadvantage, a bioconversion production method by microorganism fermentation was developed. A bioconversion reaction by a microorganism has already proved to be stereospecific and regiospecific. Accordingly, for the production of an activated vitamin D3, a conventional organic synthesis method can be replaced by an economical method by bioconversion using a microorganism's hydroxylation function.

However, in a conventional bioconversion method by microorganism fermentation, several disadvantages as described below were found.

First, since the production method is carried out by microorganism culture, there is a possibility of contamination. Also, as a production scale is enlarged, the possibility is increased. Especially, as a culture period is prolonged, an exposure to contamination becomes serious. Since such contamination occurs after the administration of vitamin D3 in concurrence with a main propagation, a cost for a precursor is consumed during the contamination. Second, a bioconversion by fermentation may cause a large range of change in production yield. This is caused by a microorganism's specific culture sensitivity and thus is inevitable. For this reason, it is required to maintain the constancy of the inside of a culture room to some extent under a predetermined condition. Accordingly, third, the overall cost for the maintenance of production facilities is increased. Fourth, productivity of the method has already reached the maximum value, and is in a stagnant state without further improvement. Thus, it cannot be determined that the method has the highest competitive power. Fifth, due to difficulty in separation and purification of impurities, an excessive separation cost may be calculated. Since only a specific material has to be separated and purified from the entire culture solution, a large-scale separation/purification is required. Thus, the cost may be proportionally increased.

Accordingly, in order to solve these disadvantages, it is urgently required to develop a novel method for producing high-purity calcitriol or calcifediol with a high yield.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

In order to solve the disadvantages of the production method through fermentation, the inventors of the present invention have researched a whole-cell biocatalytic reaction, instead of a fermentative method, as a bioconversion method. As a result, it was found that *Pseudonocardia autotrophica* ID9302, that is, a microorganism according to the present invention, has a biocatalytic function for producing calcitriol and calcifediol. Then, they have completed the present invention by developing a buffer composition for highly increasing the productivity of calcitriol and calcifediol.

Accordingly, an object of the present invention is to provide a buffer composition for promoting production of calcitriol or calcifediol consisting of 0.01 to 0.3% (w/v) at least one metallic compound selected from the group consisting of $FeCl_2$, $FeCl_3$, $FeSO_4$, $MnCl_2$, and $ZnSO_4$, 1 to 10% (w/v) of at least one organic solvent selected from the group consisting of ethanol, methanol, acetone, and dimethyl sulfoxide (DMSO), 0.1 to 5% (w/v) of cyclodextrin, 0.01 to 1% (w/v) of tris(hydroxymethyl)aminomethane, 0.01 to 1% (w/v) of sodium succinate, 0.01 to 1% (w/v) of sodium chloride, 0.001 to 0.5% (w/v) of magnesium chloride, and a residual quantity of water.

Another object of the present invention is to provide a method for producing calcitriol or calcifediol, the method comprising the steps of: culturing *Pseudonocardia autotrophica*, collecting microbial cells from the culture solution, and mixing the collected microbial cells, vitamin D3, and the buffer composition for promoting production of calcitriol or calcifediol.

To achieve the above object, the present invention provides a buffer composition for promoting production of calcitriol or calcifediol consisting of 0.01 to 0.3% (w/v) at least one metallic compound selected from the group consisting of $FeCl_2$, $FeCl_3$, $FeSO_4$, $MnCl_2$, and $ZnSO_4$, 1 to 10% (w/v) of at least one organic solvent selected from the group consisting of ethanol, methanol, acetone, and dimethyl sulfoxide (DMSO), 0.1 to 5% (w/v) of cyclodextrin, 0.01 to 1% (w/v) of tris(hydroxymethyl)aminomethane, 0.01 to 1% (w/v) of sodium succinate, 0.01 to 1% (w/v) of sodium chloride, 0.001 to 0.5% (w/v) of magnesium chloride, and a residual quantity of water.

To achieve the other object, the present invention provides a method for producing calcitriol or calcifediol, the method comprising the steps of: culturing *Pseudonocardia autotrophica*, collecting microbial cells from the culture solution, and mixing the collected microbial cells, vitamin D3, and the buffer composition for promoting production of calcitriol or calcifediol.

DETAILED DESCRIPTION OF THE DISCLOSURE

Figure 1:
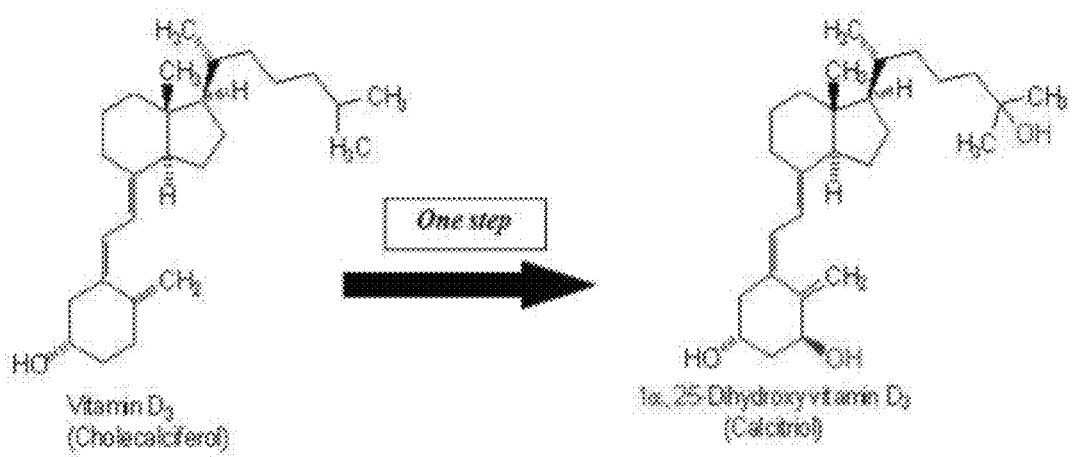
FIG. 1 is a view showing a comparison of a calcitriol production process through organic synthesis from cholesterol, to a calcitriol production process by a biocatalyst from vitamin D3.
Figure 1:
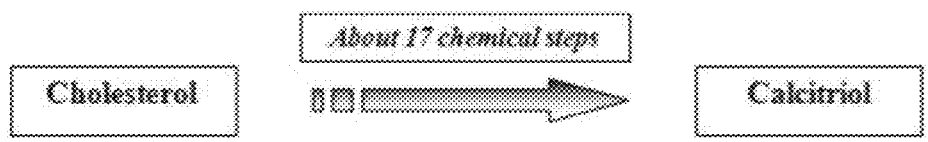

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

It is characteristic that the composition according to the present invention includes a metallic compound, an organic solvent, cyclodextrin, tris(hydroxymethyl)aminomethane, sodium succinate, sodium chloride, magnesium chloride, and water.

The composition of the present invention mainly includes tris(hydroxymethyl)aminomethane, sodium succinate, sodium chloride, and magnesium chloride, thereby forming an environment allowing microbial cells to be stably survived. There is no specific limitation in concentrations of tris(hydroxymethyl)aminomethane, sodium succinate, sodium chloride, and magnesium chloride of the inventive composition as long as a calcitriol or calcifediol production promoting effect of the inventive composition is not reduced. Preferably, tris(hydroxymethyl)aminomethane may be added in a concentration of 0.01 to 1% (w/v), sodium succinate may be added in a concentration of 0.01 to 1% (w/v), sodium chloride may be added in a concentration of 0.01 to 1% (w/v), and magnesium chloride may be added in a concentration of 0.001 to 0.5% (w/v). Most preferably, tris(hydroxymethyl)aminomethane may be added in a concentration of 0.12 to 0.61% (w/v), sodium succinate may be added in a concentration of 0.16 to 0.8% (w/v), sodium chloride may be added in a concentration of 0.06 to 0.18% (w/v), and magnesium chloride may be added in a concentration of 0.006 to 0.05% (w/v).

Cyclodextrin of the present invention is a ring-shaped non-reducing sugar with several α-1,4 linked glucose molecules. It forms a host-guest inclusion complex due to its hydrophobic inside and hydrophilic outside, thereby stabilizing vitamin D3 as a substrate within a buffer. Cyclodextrin of the present invention may be α-cyclodextrin, β-cyclodextrin, γ-cyclodextrin, or methyl-β-cyclodextrin, and most preferably may be a β-cyclodextrin. There is no specific limitation in a concentration of cyclodextrin of the present invention as long as a calcitriol or calcifediol production promoting effect of the inventive composition is not reduced. Preferably, the concentration of cyclodextrin may range from 0.1 to 5% (w/v), and more preferably from 0.25 to 1% (w/v).

An organic solvent of the present invention increases the solubility of a substrate (an insoluble material). The organic solvent of the present invention may be ethanol, methanol, acetone or dimethyl sulfoxide (DMSO), and most preferably may be methanol. There is no specific limitation in a concentration of the organic solvent of the present invention as long as a calcitriol or calcifediol production promoting effect of the inventive composition is not reduced. Preferably, the concentration may range from 1 to 10% (w/v), and more preferably from 2.5 to 10% (w/v).

A metallic compound of the present invention activates electron transfer, thereby increasing the efficiency of conversion from a substrate to calcitriol or calcifediol. There is no limitation in the metallic compound of the present invention as long as it does not reduce a calcitriol or calcifediol production promoting effect of the inventive composition, and is a compound generating metallic ions. Preferably, the metallic compound may be $FeCl_2$, $FeCl_3$, $FeSO_4$, $MnCl_2$, or $ZnSO_4$, and most preferably may be $MnCl_2$. There is no specific limitation in a concentration of the metallic compound of the present invention as long as a calcitriol or calcifediol production promoting effect of the inventive composition is not reduced. Preferably, the concentration may range from 0.01 to 0.3% (w/v), and more preferably from 0.01 to 0.03% (w/v).

The calcitriol or calcifediol production promoting buffer composition of the present invention has a high calcitriol or calcifediol production promoting effect.

Meanwhile, a method for producing calcitriol or calcifediol, according to the present invention, comprises the steps of: (a) culturing *Pseudonocardia autotrophica*, (b) collecting microbial cells from the culture solution, and (c) mixing the collected microbial cells, vitamin D3, and the buffer composition for promoting production of calcitriol or calcifediol.

In step (a), *Pseudonocardia autotrophica* is cultured. In the present invention, the culture of *Pseudonocardia autotrophica* may employ a conventionally used microorganism inoculation/culture method. The inoculation is carried out by adding pre-cultured *Pseudonocardia autotrophica* in an appropriate amount to a culture medium, wherein the *Pseudonocardia autotrophica* has been pre-cultured so that *Pseudonocardia autotrophica* can be sufficiently propagated under a culture condition. In the inoculation of *Pseudonocardia autotrophica*, the pre-cultured *Pseudonocardia autotrophica* culture solution may be added in an amount of 1 to 5% (v/v) to a culture medium. The culture of *Pseudonocardia autotrophica* may be carried out through a medium and culture conditions, known in the art. Such a process may be easily adjusted by a person skilled in the art according to a selected strain. These various methods are disclosed in various literatures (e.g., James et al., Biochemical Engineering, Prentice-Hall International Editions). They are divided into a suspension culture method and an attachment culture method according to a cell growth mechanism, and also divided into a batch culture, a fed-batch, and a continuous culture according to a culture method.

As a culture medium, a medium including a carbon source, a nitrogen source, vitamins, and minerals may be used. In the medium for producing cultures of the present invention, the carbon source may be at least one selected from the group including glucose, sucrose, maltose, fructose, lactose, xylose, galactose, arabinose, and a combination thereof, and more preferably may be glucose. In the medium for producing cultures of the present invention, the nitrogen source may be at least one selected from the group including yeast extract, soytone, peptone, beef extract, tryptone, casitone, and a combination thereof, and more preferably may be yeast extract.

In step (a), *Pseudonocardia autotrophica* may include any one of the same kind of microorganisms, and may include one from all of subspecies and varieties of *Pseudonocardia autotrophica*. Preferably, *Pseudonocardia autotrophica* ID9302 may be used.

*Pseudonocardia autotrophica* ID9302, which is a biocatalyst according to the present invention, was deposited to Korea Research Institute of Bioscience and Biotechnology Biological Resource Center (KCTC) on Jun. 7, 2001 (deposition no: KCTC 1029BP).

In step (b), from the culture solution, microbial cells are collected. There is no limitation in the microbial cell collection method in the present invention as long as it is a conventionally used method for collecting microbial cells in a live state. Preferably, a centrifuge method may be used. Preferably, in order to remove nutritive components within the culture solution, the collected microbial cells may be washed with a buffer. The washing buffer may be preferably a buffer composition promoting calcitriol or calcifediol production according to the present invention.

In step (c), the collected microbial cells, vitamin D3, and the inventive buffer composition for promoting production of calcitriol or calcifediol are mixed. In step (c), the collected microbial cells are dissolved in the inventive buffer composition for promoting production of calcitriol or calcifediol while performing a function of converting vitamin D3 (as a substrate) into calcitriol or calcifediol.

In step (c), the mixing may be carried out in any order or by any method as long as calcitriol or calcifediol is produced by the inventive producing method. In one example, vitamin D3 may be firstly dissolved in a known solvent, and then mixed with the inventive calcitriol or calcifediol production promoting buffer composition including the collected microbial cells dissolved therein. In another example, the inventive calcitriol or calcifediol production promoting material may be firstly dissolved in vitamin D3, and a known solvent, and then mixed with the inventive calcitriol or calcifediol production promoting buffer composition including the collected microbial cells dissolved therein. There is no limitation in the solvent as long as it can help the dissolution of the known vitamin D3. For example, the solvent may be methanol, ethanol, acetone, DMSO, or a mixture thereof. Meanwhile, the inventive calcitriol or calcifediol production promoting material may be, for example, cyclodextrin, cremophore, polyethylene glycol, dipropylene glycol, tween 85, tween 80, or PEG 300.

Also, vitamin D3 in a total amount required for the reaction may be administered at once, or several divided times. Otherwise, vitamin D3 may be continuously administered while the predetermined concentration of vitamin D3 within the mixture is maintained. The mixing state may be variously maintained in consideration of the efficiency in the conversion of vitamin D3 into the inventive calcitriol or calcifediol by the collected microbial cells, and the survival rate of the microbial cells. Preferably, the mixing state may be maintained for to 10 days. During the mixing state period, a pH, a stirring state, and an air current amount may be appropriately maintained in order to efficiently produce calcitriol or calcifediol, or to maintain the survival of microbial cells. Such a process may be easily adjusted by a person skilled in the art.

In Example 1, GAC (growth-arrested cells) were prepared by culturing *Pseudonocardia autotrophica* ID9302 and collecting microbial cells through centrifugation. They were used to measure productivities of calcitriol and calcifediol by vitamin D3 in various kinds of buffer compositions.

As a result, it was found that productivities of calcitriol and calcifediol were the highest in a TSSM buffer including 25 mM tris(hydroxymethyl) aminomethane, 25 mM sodium succinate, 20 mM sodium chloride, and 4 mM magnesium chloride (see Example 1).

Then, tests for adding various materials for improving the productivity of calcitriol and calcifediol were carried out by using the TSSM buffer as a basic buffer.

In Example 2, a change in productivities of calcitriol and calcifediol was measured by adding cyclodextrin at varying concentrations.

As a result, it was found that cyclodextrin increased the production yields of calcitriol and calcifediol, and especially, the addition of β-cyclodextrin increased the production yields (see Example 2).

In Example 3, a change in productivities of calcitriol and calcifediol was measured by adding various organic solvents at varying concentrations.

As a result, it was found that the administration of an organic solvent increased the production yields of calcitriol and calcifediol, and especially, the addition of methanol increased the production yields (see Example 3).

Also, it was found that when both cyclodextrin and an organic solvent were added, the production yields were remarkably higher than those in the administration of any one of cyclodextrin and an organic solvent (see Example 4).

In Example 6, a change in productivities of calcitriol and calcifediol was measured by adding various metallic compounds at varying concentrations.

As a result, it was found that when $CuCl_2$, $CuSO_4$, $CoCl_2$, and $CoSO_4$ were used, the biocatalytic reaction was not sufficiently performed irrespective of concentrations, or the production yields of calcifediol and calcitriol were reduced.

Meanwhile, it was found that the administration of $FeCl_2$, $FeCl_3$, $FeSO_4$, $ZnSO_4$ or $MnCl_2$ increased the production yields of calcifediol and calcitriol. Especially, the administration of $ZnSO_4$ or $MnCl_2$ highly increased the production yields (see Example 6).

In Example 7, a change in productivities of calcitriol and calcifediol according to a change in pH was measured.

As a result, it was found that the production yields of calcitriol and calcifediol were changed according to a pH, and the production yields were the highest at a pH ranging from 7.0 to 7.4 (see Example 7).

In Example 8, calcitriol or calcifediol was mass-produced in a 75 l fermentation tank by variously adjusting an organic solvent and a metallic compound in the inventive calcitriol or calcifediol production promoting buffer composition obtained in the above described Examples.

As a result, in the inventive calcitriol or calcifediol production promoting buffer composition, in a case of $FeCl_2$, $FeCl_3$, and $FeSO_4$, at a concentration of 0.01%, calcitriol production yields were 53.12 mg/L, 60.8 mg/L, and 62.42 mg/L, and in a case of $ZnSO_4$, at a concentration of 0.01%, a calcitriol production yields was 77.18 mg/L. Especially, in a case of $MnCl_2$, at a concentration of 0.03%, a calcitriol production yield was 90.12 mg/L, and a calcifediol production yield was 166.87 mg/L (see Example 8).

Accordingly, it was found that the inventive composition including $FeCl_2$, $FeCl_3$, $FeSO_4$, $ZnSO_4$ and $MnCl_2$ showed a high calcitriol or calcifediol productivity.

Also, when a mass-production was carried out by varying the kinds of an organic solvent, ethanol showed a calcitriol production yield of 48.45 mg/L, and acetone and DMSO showed calcitriol production yields of 74.87 mg/L and 70.85 mg/L, respectively, and calcifediol production yields of 156.37 mg/L and 141.81 mg/L, respectively. Especially, methanol showed a calcitriol production yield of 90.12 mg/L, and a calcifediol production yield of 166.87 mg/L (see Example 9). Accordingly, it can be seen that the inventive composition including methanol, ethanol, acetone, and DMSO showed a high calcitriol or calcifediol productivity.

In Example 10, calcitriol or calcifediol was produced in a 75 l fermentation tank according to the inventive calcitriol or calcifediol producing method by using the inventive calcitriol or calcifediol production promoting buffer composition obtained in the above described Examples. Then, the produced calcitriol or calcifediol was separated and purified.

It was found that when calcitriol or calcifediol was produced by the inventive method, on the $7^{th}$ day, the productivity of calcitriol was the highest (91.23 mg/L), and the productivity of calcifediol was 168.24 mg/L (Example 10).

The resultant product was collected, and microbial cells were removed from the product. Then, vitamin D3, calcifediol, and calcitriol were separated and purified.

As a result, 7.6 g of calcifediol with a purity of 90% or more and 2.2 g of calcitriol with a purity of 99% were obtained (see Example 11).

As described above, in the inventive calcitriol or calcifediol production promoting buffer composition or the inventive production method, after removal of a culture solution, the reaction of vitamin D3 with microbial cells is carried out in a buffer state. Thus, it is possible to reduce the amount of other metabolites generated from a culture environment, increase the yield of bioconversion into a required target material, and highly increase the efficiency of separation/purification due to a small amount of generated impurities. As a result, it is possible to improve the quality of a raw material, and reduce a cost for separation/purification. Furthermore, it is advantageous in the production of calcitriol or calcifediol since gross production of calcitriol can be increased through a high-concentration reaction.

Accordingly, the present invention provides a buffer composition promoting calcitriol or calcifediol production, and a method for producing calcitriol or calcifediol using the same. In the inventive production method, the production yield of calcitriol or calcifediol is high, and the bioconversion is carried out in a catalytic reaction system instead of in a microorganism culture system. Thus, it is not required to maintain a sterile state. Also, the separation/purification following the completion of a biocatalytic reaction can be carried out in a cleaner state than the microorganism culture method. Accordingly, there is an advantage in that a cost required for separation is low and the quality is improved. Furthermore, the inventive calcitriol or calcifediol production promoting buffer composition can provide a high productivity of calcitriol or calcifediol.

EXAMPLES

Hereinafter, the present invention will be described in detail with reference to Examples. However, the following examples are only for illustrative purposes and are not intended to limit the scope of the invention.

Example 1

Determination of a Biocatalytic Reaction Buffer for Producing Calcitriol

The productivity of calcitriol was tested in various kinds of buffers so that GAC (growth-arrested cells) as a biocatalyst can introduce a hydroxylic group to vitamin D3 through a biocatalytic reaction.

<1-1> Preparation of *Pseudonocardia autotrophica* ID9302 as GAC

For the use as a biocatalyst for producing calcifediol and calcitriol of the present invention, *Pseudonocardia autotrophica* ID9302 (hereinafter, referred to as ID9302) strain was cultured in a medium under a proper condition (dried yeast 0.4%, glucose 1%, starch 1%, fish meal 1%, sodium chloride 0.2%, potassium dihydrogen phosphate 0.01%, beef extract 0.1%, sodium fluoride 0.01%, and calcium carbonate 0.2%, a sterilized liquid medium with pH 7.0), and then microbial cells were collected through centrifugation. The collected microbial cells were washed with a biocatalytic reaction buffer (see Table 1) to be used for the following experiment, to completely remove nutritive components within the culture solution. Then, GAC (hereinafter, referred to as ID9302 GAC) for the biocatalytic reaction to be carried out in the next step were prepared.

<1-2> Measurement of Productivity of Calcitriol and Calcifediol by ID9302 GAC According to a Buffer Composition GAC as a biocatalyst, prepared by 50 ml of main culture were re-dissolved in 50 ml of various buffers noted in Table 1. The solution was placed in a 250 ml erlenmeyer flask, and 3000 of 5% vitamin D3 solution (in ethanol) was added thereto. Then, the mixture was subjected to a shake-reaction for 9 days under the same condition. On the seventh day and the ninth day, 3 ml of the culture solution was collected, and 6 ml of an extraction solvent (methylene chloride/methanol=1/1) was added thereto, followed by mixing for 30 min. Then, an organic solvent layer was collected, concentrated, and was subjected to HPLC analysis so as to measure the yield of the biocatalytic reaction, and the productivity of calcitriol and calcifediol.

UV patterns corresponding to pure products of calcitriol and calcifediol were compared to peaks showing RT so as to determine the productivity. In the HPLC analysis, a column was J'sphere ODS-H80 (150×4.6 mm I.D.), a moving phase was a mixed solvent of 450 ml of 0.1% tris(hydroxymethyl) aminomethane (THAM) and 550 ml of acetonitrile, with a phosphoric acid-adjusted pH of 7.2~7.3, a moving rate was 1 ml/min, and a photodiode array detector was used for the detection.

TABLE 1

Effect on a biocatalytic reaction by various kinds of buffers

| Kind of buffer | Amount of produced calcitriol (mg/L) | |
|---|---|---|
| | 7$^{th}$ day from culture | 9$^{th}$ day from culture |
| Saline solution | 0.50 | 0.00 |
| PBS buffer, pH 7.2 | 0.26 | 0.00 |
| 20 mM Maleate buffer, pH 6.5 | 0.67 | 0.76 |
| 15 mM Acetate buffer, pH 5.0 | 0.05 | 0.09 |
| TSSM buffer, pH 7.2 | 1.65 | 1.41 |

* TSSM buffer: 25 mM Trizma base, Tris(hydroxymethyl)aminomethane), 25 mM sodium succinate, 20 mM sodium chloride, 4 mM magnesium chloride As a result, as noted in Table 1, it was found that when TSSM buffer was used, the biocatalytic capability for introducing a hydroxylic group to vitamin D3 by ID9302 was the highest.

Also, it was found that Maleate buffer was a relatively superior buffer for ID9302 as a biocatalyst although its calcitriol productivity was lower than that (1.65 mg/L) in TSSM buffer.

TSSM buffer includes Trizma base with a high buffering effect of pH, NaCl with a high ionic strength, sodium succinate contributing metabolism, magnesium ions as cofactor of p450 hydroxylase, etc., and showed an especially superior productivity with 10~50 mM Trizma base, 10~50 mM sodium succinate, 10~30 mM sodium chloride, 1~8 mM magnesium chloride, and pH of 7.0 to 7.4. Accordingly, TSSM buffer was determined as a buffer for a biocatalytic reaction in p450 hydroxylase reaction system.

Example 2

Effect on a Biocatalytic Reaction by Cyclodextrin

Under the same biocatalytic reaction condition as that determined by Example 1, a bioconversion test was carried out. To 50 ml of TSSM buffer, ID9302 GAC as a biocatalyst was added, and various cyclodextrins were introduced thereto with concentrations of 0.25%, 0.5%, and 1%. Also, 300 μl of 5% vitamin D3 ethanol solution was placed in a erlenmeyer flask. Then, a bioconversion test was carried out in such a manner that the mixture was subjected to a shake-reaction for 9 days. On the 5$^{th}$ day, the 7$^{th}$ day, and the 9$^{th}$ day, 3 ml of the reaction test sample was collected, and was subjected to extraction, concentration, and HPLC analysis in the same manner as that described in Example 1-2.

Figure 2:
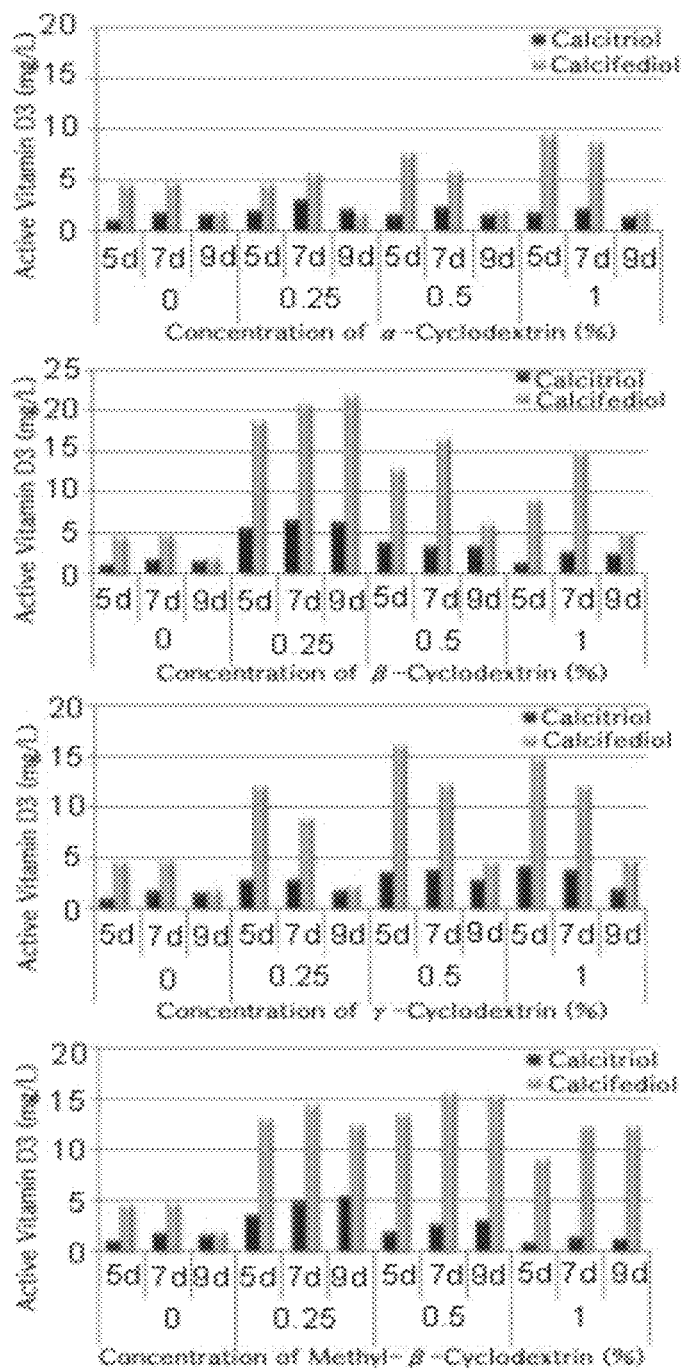
FIG. 2 is a graph showing that calcifediol and calcitriol are produced, in which cyclodextrin has an effect on a biocatalytic reaction while bio-converting vitamin D3 (number d: a period (days) from the start of the reaction)

Through the final HPLC analysis, it was found that cyclodextrin changed conditions of TSSM buffer, and thus increased ID9302 GAC (as a biocatalyst)'s yield for introducing a hydroxylic group to vitamin D3 (see FIG. 2). The productivity of calcitriol and calcifediol according to the kind, concentration, and culture time of cyclodextrin was summarized in Table 2 below.

TABLE 2

Effect on bioconversion by proper concentrations of various kinds of cyclodextrins

| | | 0% | | | 0.25% | | | 0.50% | | | 1% | | |
|---|---|---|---|---|---|---|---|---|---|---|---|---|---|
| | | 5 d | 7 d | 9 d | 5 d | 7 d | 9 d | 5 d | 7 d | 9 d | 5 d | 7 d | 9 d |
| calcitriol mg/L | α-CD | 1.03 | 1.64 | 1.45 | 1.86 | 3 | 2.05 | 1.44 | 2.3 | 1.47 | 1.69 | 1.99 | 1.36 |
| | β-CD | 1.03 | 1.64 | 1.45 | 5.5 | 6.22 | 6 | 3.69 | 3.25 | 3.22 | 1.13 | 2.49 | 2.26 |
| | γ-CD | 1.03 | 1.64 | 1.45 | 2.83 | 2.79 | 1.66 | 3.43 | 3.57 | 2.69 | 4.09 | 3.71 | 1.91 |
| | M-CD | 1.03 | 1.64 | 1.45 | 3.46 | 4.71 | 5.16 | 1.89 | 2.59 | 2.86 | 0.74 | 1.42 | 1.09 |
| calcifediol mg/L | α-CD | 4.52 | 4.69 | 1.94 | 4.6 | 5.53 | 1.77 | 7.62 | 5.69 | 2.09 | 9.36 | 8.55 | 2.11 |
| | β-CD | 4.52 | 4.69 | 1.94 | 18.62 | 20.5 | 21.63 | 12.8 | 16.24 | 6 | 8.96 | 14.68 | 4.89 |
| | γ-CD | 4.52 | 4.69 | 1.94 | 11.91 | 8.79 | 2.19 | 15.83 | 12.13 | 4.62 | 14.72 | 11.97 | 4.73 |
| | M-CD | 4.52 | 4.69 | 1.94 | 12.88 | 14.28 | 12.29 | 13.39 | 15.36 | 15.13 | 8.9 | 12.23 | 12.23 |

It was found that when α-cyclodextrin was introduced to TSSM buffer, the production yield of calcitriol at a concentration of 0.25% was increased 1.83 times compared to that of a control group (TSSM buffer with no addition of cyclodextrin, see Table 1). Also, calcifediol as a precursor of calcitriol was increased according to the concentration increase of α-cyclodextrin, and its productivity at a concentration of 1% was increased 1.82 times.

It was found that when β-cyclodextrin (β-CD) was introduced to TSSM buffer, the best bioconversion result was shown at 0.25%. It can be found that the production yield of calcitriol was increased 3.79 times compared to that of a control group. Also, it was found that the productivity of calcifediol was increased 4.37 times at a concentration of 0.25% of β-cyclodextrin.

In a case of γ-cyclodextrin (γ-CD), it was found that the production yield of calcitriol was increased 1.7 times, 2.18 times, and 2.26 times in proportion to the administration concentration increase of 0.25%, 0.5%, and 1%, and the production yield of calcifediol was highly increased.

Methyl-β-cyclodextrin (M-CD) (as a precursor of β-cyclodextrin) showed the highest calcitriol production yield at 0.25%, which is 2.87 times higher that that of a control group. Then, at following concentrations, the calcitriol productivity was suddenly decreased while the production yield of calcifediol was maintained high.

From the results as described above, in the present invention, it was found that TSSM buffer administered with cyclodextrin at a proper concentration (hereinafter, referred to as 'TSSMC buffer') showed a high bioconversion yield of vitamin D3, compared to a control group (TSSM buffer) with no administration of cyclodextrin, and thus the production yields of calcitriol and calcifediol were increased.

Example 3

Effect on a Biocatalytic Reaction by a Specific Organic Solvent

Based on the biocatalytic reaction conditions determined from Example 1, an effect on a biocatalytic reaction by an organic solvent, and production effects of calcitriol and calcifediol were tested. Under the biocatalytic reaction conditions of Example 1, 4 kinds of organic solvents noted in Table 3 were administered in such a manner that final concentrations can reach 2.5%, 5%, 10%, 20%, and 30%, respectively. The test was carried out under the same condition as that in the shake-reaction in Example 2. On the $8^{th}$ day of the biocatalytic reaction, the reaction was finished, and HPLC quantitative analysis was carried out in the same manner as that in Example 1-2.

TABLE 3

Effect on a biocatalytic reaction by a specific organic solvent

| Organic solvent concentration | Amount of produced calcitriol (mg/L) | | | | Amount of produced calcifediol (mg/L) | | | |
|---|---|---|---|---|---|---|---|---|
| (%) | ethanol | methanol | acetone | DMSO | ethanol | methanol | acetone | DMSO |
| 0 | 1.66 | 1.66 | 1.66 | 1.66 | 5.53 | 5.53 | 5.53 | 5.53 |
| 2.5 | 0.74 | 4.45 | 3.54 | 3.39 | 36.34 | 25.91 | 30.24 | 28.32 |
| 5 | 0.30 | 4.77 | 3.91 | 3.87 | 30.66 | 28.48 | 31.05 | 25.83 |
| 10 | 0.02 | 5.84 | 4.14 | 4.03 | 1.97 | 33.90 | 36.44 | 25.36 |
| 20 | 0.00 | 0.00 | 0.66 | 1.66 | 1.03 | 1.36 | 4.05 | 0.90 |
| 30 | 0.00 | 0.00 | 0.04 | 0.08 | 0.49 | 0.00 | 2.04 | 0.23 |

From the analysis result, it was found that ethanol did not show bioconversion of calcitriol (as a target material) at all according to the administration concentration increase of ethanol, compared to a control group with no ethanol. Meanwhile, at 2.5%, and 5% of ethanol, the production yield of calcifediol was increased 6.57 times and 5.54 times, compared to that of a control group.

It was found that methanol did not show bioconversion at all at an administration concentration of 20% or more, and then at 2.5% to 10% of administration concentrations of methanol, the production yield of calcitriol was increased up to 3.52 times compared to that of a control group. Also, the production yield of calcifediol was increased 6 times or more.

In a case of acetone and Dimethyl Sulfoxide (DMSO), the production yield of calcitriol was increased 2 to 2.5 times, and the production yield of calcifediol was increased 5.5 to 6.5 times, compared to those of a control group.

Figure 3:
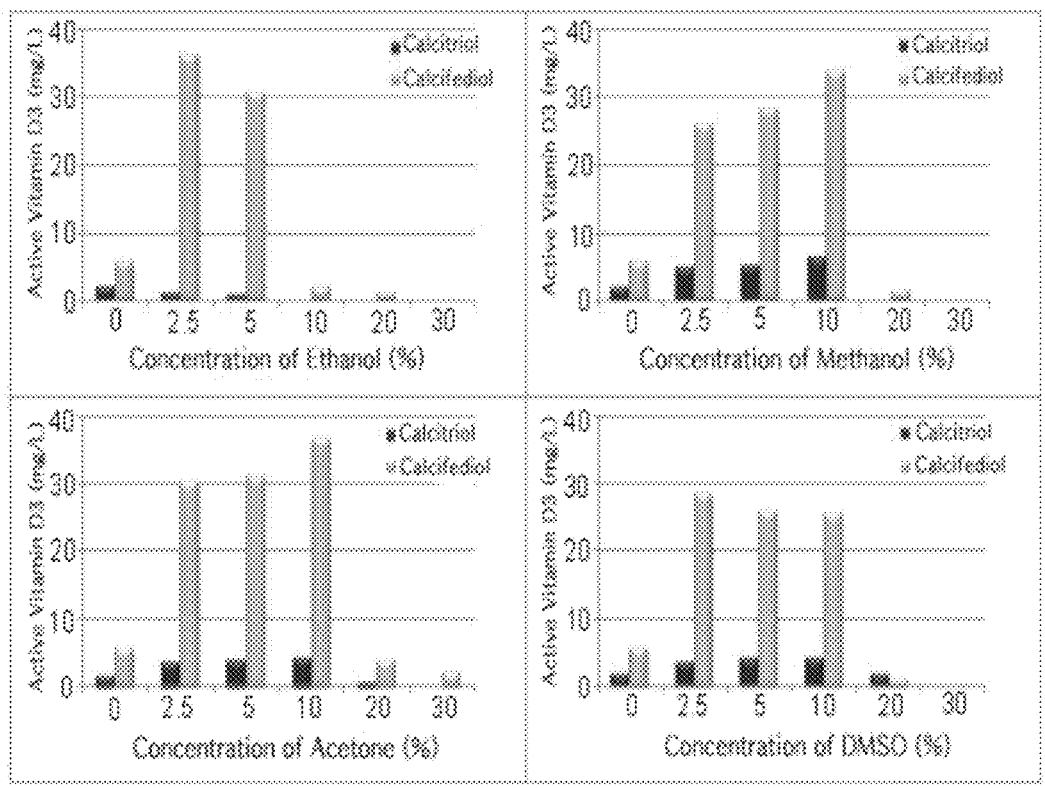
FIG. 3 is a graph showing that calcifediol and calcitriol are produced, in which a specific organic solvent has an effect on a biocatalytic reaction while bio-converting vitamin D3.

From the results as described above, it can be seen that the introduction of an organic solvent at a predetermined concentration to a biocatalytic reaction increases the solubility of vitamin D3 (insoluble material), thereby increasing the production yield of calcitriol (see FIG. 3).

Example 4

Effect on a Biocatalytic Reaction by a Mixing Condition of Cyclodextrin and Organic Solvent 0.25% β-cyclodextrin, which showed the highest bioconversion effect in Example 2, was introduced to a TSSM buffer, thereby providing a TSSMC buffer. The TSSMC buffer was used as a basic biocatalytic reaction buffer. In consideration of a valid effect on the bioconversion by an organic solvent, determined in Example 3, an organic solvent was introduced, at a concentration from 2.5% to 10%, to the biocatalytic reaction buffer. Then, according to the mixing of cyclodextrin and organic solvent, the effect on the yield of bioconversion was tested. GAC preparation, shake-reaction conditions, and HPLC analysis were the same as those in Example 1.

Figure 4:
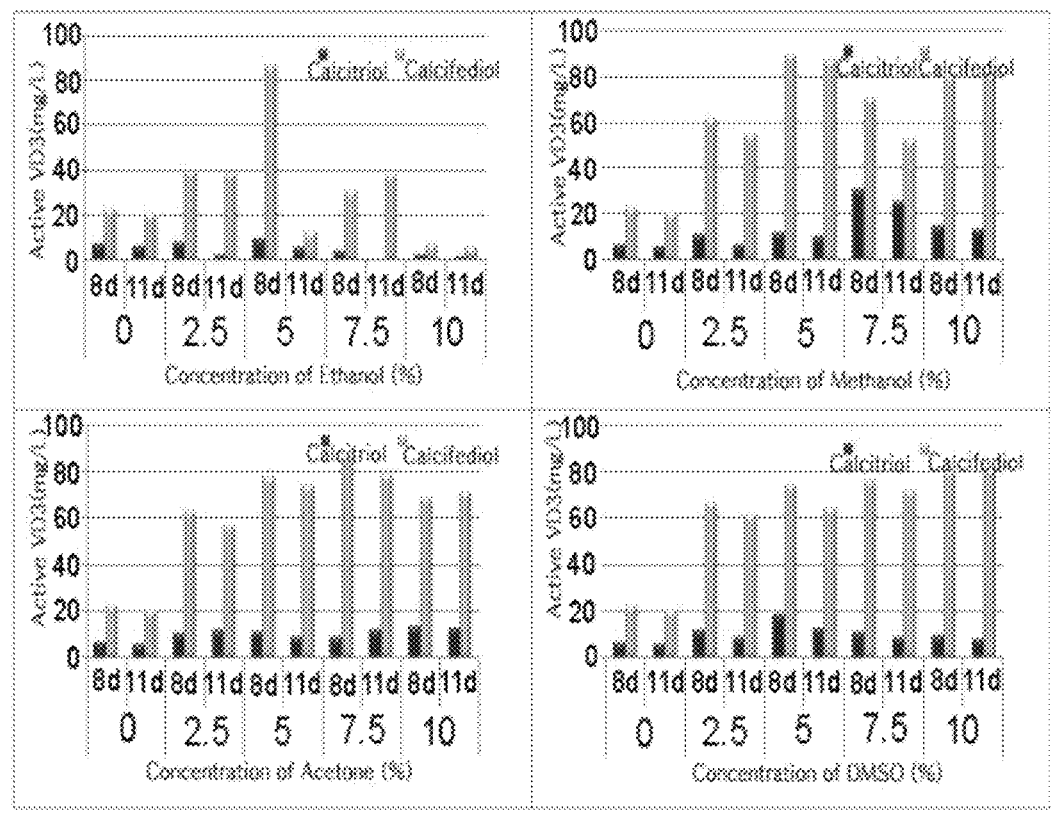
FIG. 4 is a graph showing that a mixing condition of β-cyclodextrin with a specific organic solvent has an effect on a biocatalytic reaction, for high productivity of calcifediol and calcitriol through bioconversion of vitamin D3 (number d: a period (days) from the start of the reaction)

As a result, the mixing of β-cyclodextrin and the organic solvent showed a positive reaction on the biocatalytic reaction. Also, when methanol was added, the production yield of calcitriol was increased, and the productivity of calcifediol (a biosynthesis precursor of calcitriol) was about 4 times higher (89.14 mg/L) that that of a control group (see FIG. 4).

TABLE 4

Results of bioconversion by the mixing of β-cyclodextrin and various kinds of organic solvents, on the $8^{th}$ day

| | | Organic solvent (%) | | | | |
|---|---|---|---|---|---|---|
| | | 0 | 2.5 | 5 | 7.5 | 10 |
| Amount of produced calcitriol (mg/L) | ethanol | 6.37 | 6.78 | 8.67 | 3.53 | 1.39 |
| | Methanol | 6.37 | 10.91 | 11.77 | 30.32 | 14.32 |
| | Acetone | 6.37 | 10.03 | 11.01 | 11.74 | 13.08 |
| | DMSO | 6.37 | 11.42 | 18.32 | 10.65 | 9.32 |
| Amount of produced calcifediol (mg/L) | Ethanol | 22.53 | 39.00 | 86.36 | 30.29 | 6.78 |
| | Methanol | 22.53 | 61.46 | 89.14 | 71.03 | 79.94 |
| | Acetone | 22.53 | 62.79 | 77.66 | 86.15 | 71.51 |
| | DMSO | 22.53 | 66.44 | 74.48 | 76.48 | 80.25 |

Like Example 3, methanol showed the highest production yield of calcitriol through the mixing with cyclodextrin. Methanol at a concentration of 2.5% showed productivity increases of calcitriol and calcifediol, and then at a methanol concentration of 7.5%, the production yield of calcitriol was increased 4.76 times, compared to that of a control group. In a case of acetone, at a concentration of 10%, the production yield of calcitriol was increased about twice compared to that of a control group, and in a case of DMSO, at a concentration of 5%, the production yield of calcitriol was increased 2.88 times compared to that of a control group. Also, in a case of ethanol, at a concentration of 5%, the productivity of calcitriol was increased 1.4 times compared to that of a control group, and the productivity of calcifediol was increased 3.8 times compared to that of a control group while in Example 3, no calcitriol was produced.

From the result as described above, it can be found that the mixing of cyclodextrin and an organic solvent showed a synergy effect on a biocatalytic reaction because cyclodextrin increases the solubility of insoluble vitamin D3, and the organic solvent increases the fat-solubility in a buffer condition. The synergy effect showed a sudden increase in the production yields of calcitriol and calcifediol. Especially, in a case of methanol at 7.5%, the production yield of calcitriol was the highest (30.32 mg/L), which was increased about 4.76 times compared to that of a control group. In a case of methanol at 5%, the production yield of calcifediol was increased about 4 times (89.14 mg/L) compared to that of a control group.

Example 5

Production of Calcifediol (Activated Vitamin D3) and Calcitriol Through a Biocatalytic Reaction in a 75 L Fermentation Tank Based on the reaction conditions determined from Examples 1 to 4, a calcifediol/calcitriol production test was carried out in which a hydroxylic group was introduced to vitamin D3 by using a biocatalyst in a 75 L fermentation tank. The culture condition was the same as that in Example 1 except that through scale-up, 2 L liquid culture solution (in a 2.5 L fermentation tank) was used for an intermediate culture, and 50 L liquid medium (in a 75 L fermentation tank) was used for a main culture. HPLC analysis was carried out in the same manner as that in Example 1-2.

After the completion of the main culture of ID9302 for 5 days, ID9302 GAC as a biocatalyst was prepared. In a 75 L fermentation tank as a reaction tank, 50 L of a TSSMC buffer including 7.5% methanol at a final concentration was placed, and ID9302 GAC was re-dissolved in the reaction buffer. 300 ml of 5% vitamin solution was prepared and introduced to a biocatalytic reaction system in equilibrium. Then, bioconversion of vitamin D3 was carried out under the condition of 28° C., 500 rpm, and 1 vvm for 10 days. For 10 days from the $3^{rd}$ day, the reaction solution was subjected to HPLC analysis, and then the productivity of calcitriol and calcifediol was tested.

Figure 5:
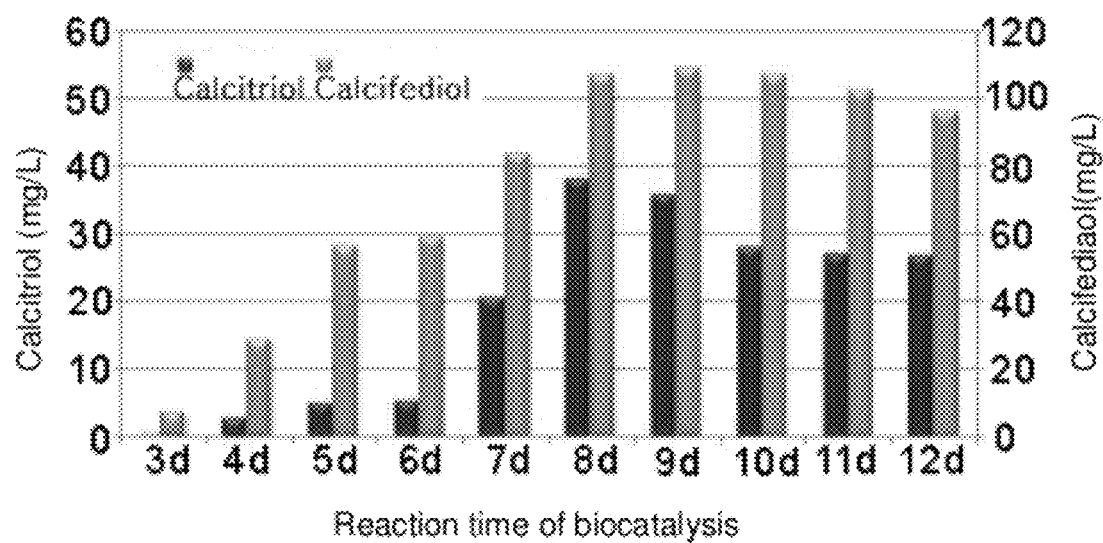
FIG. 5 is a graph showing that an activated vitamin D3 derivative is produced from vitamin D3 through a biocatalytic reaction in a 75 l fermentation tank (number d: a period (days) from the start of the reaction)

As a result, on the $3^{rd}$ day of a biocatalytic reaction, the production of calcifediol as a precursor of calcitriol was started. Then, on the $4^{th}$ to $5^{th}$ day of the reaction, production of calcifediol was suddenly increased, and at the same time, the production of calcitriol was in actuality started. On the $7^{th}$ day of the biocatalytic reaction, the production of calcitriol and calcifediol was suddenly increased, on the $8^{th}$ day of the biocatalytic reaction, the productivity of calcitriol was the highest (38.1 mg/L), and on the $9^{th}$ day of the reaction, the productivity of calcifediol was 109 mg/L. Compared to that on the $3^{rd}$ day of reaction, the productivity of calcitriol was increased 38 times, and the productivity of calcifediol was increased 15 times. On the $12^{th}$ day of the biocatalytic reaction from the maximum production, the productivities of the two materials were slowly decreased (see FIG. 5).

Accordingly, it can be found that when a biocatalyst was prepared by ID9302 and the reaction was carried out in a 75 L fermentation tank, it is possible to introduce a hydroxylic group to vitamin D3 and at the same time to achieve a high productivity of calcitriol and calcifediol.

Example 6

Effect on a Biocatalytic Reaction by a Metallic Material

In bioconversion of vitamin D3 into calcifediol and calcitriol, electron transfer is important. When a TSSMC buffer is added with a metallic material, electrons coming from the metallic material can facilitate the electron transfer. This may increase enzyme activity, thereby increasing a bioconversion ratio.

Based on the biocatalytic reaction condition determined in Example 4, a metallic material's effect on a biocatalytic reaction, and a production effect of calcifediol and calcitriol were tested.

Under a biocatalytic reaction condition of a TSSMC buffer further including 7.5% methanol, 9 kinds of metallic materials noted in Table 5 were administered in such a manner that their concentrations can be 0.01%, 0.03%, and 0.06%. The test was carried out under the same condition as that in the shake-reaction of Example 2, and then on the $7^{th}$ day and the $9^{th}$ day of the biocatalytic reaction, HPLC quantitative analysis was carried out in the same manner as that in Example 1-2.

According to the result of the analysis, when $CuCl_2$, $CuSO_4$, $CoCl_2$, and $CoSO_4$ were used, the biocatalytic reaction was not sufficiently performed irrespective of concentrations. As a result, the production yields of calcifediol and calcitriol were reduced. Also, $FeCl_2$ and $FeCl_3$ did not show an increase in production yields of calcifediol and calcitriol. Meanwhile, in a case of $FeSO_4$ at 0.06%, calcitriol was increased 1.14 times compared to that of a control group.

In a case of $MnCl_2$, at 0.06%, production yields of calcifediol and calcitriol were decreased, and at 0.01%, the production yield of calcitriol was increased 1.15 times compared to that of a control group. Also, at a concentration of 0.03%, production yields of calcitriol and calcifediol were increased 1.83 times, and 1.52 times, respectively. $MnCl_2$ showed the highest increase in the production yield, compared to other metallic materials.

Figure 6:
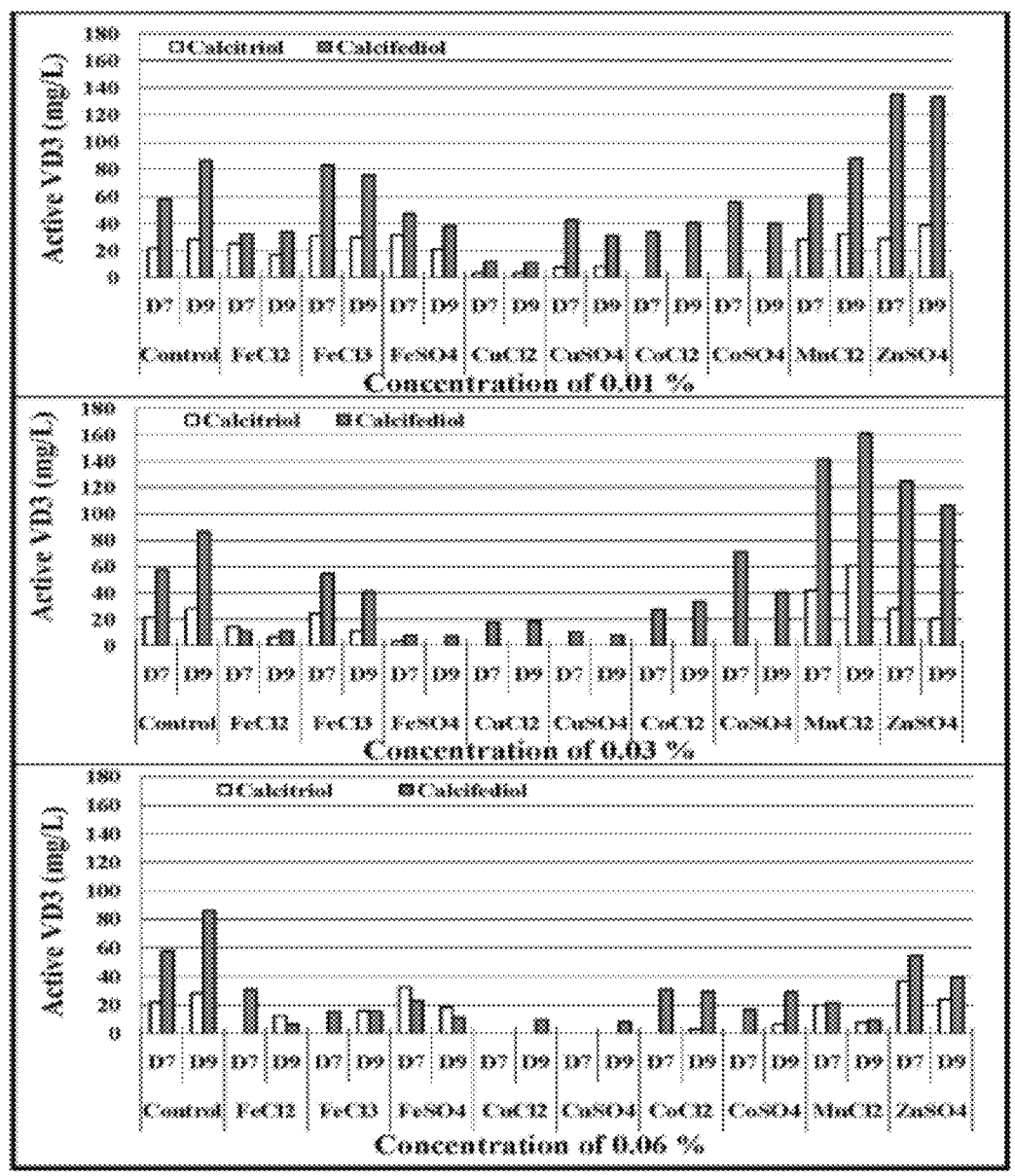
FIG. 6 is a graph showing that calcifediol and calcitriol are produced, in which a metallic compound has an effect on a biocatalytic reaction while bio-converting vitamin D3 (number d: a period (days) from the start of the reaction)

In a case of $ZnSO_4$, at 0.01%, a production yield of calcitriol was similar to that of a control group, while a production yield of calcifediol was increased 1.34 times. At 0.06%, compared to that of a control group, the production yield of calcitriol was increased 1.3 times (see FIG. 6).

From the results as described above, it can be found that introduction of some metallic materials to a biocatalytic reaction increased a bioconversion effect, thereby increasing the production yields of calcifediol and calcitriol.

TABLE 5

Effect on a biocatalytic reaction by a metallic material

| Metallic compound | Reaction time | Amount of produced calcitriol (mg/L) Concentration (%) | | | | Amount of produced calcifediol (mg/L) Concentration (%) | | | |
|---|---|---|---|---|---|---|---|---|---|
| | | 0 | 0.01 | 0.03 | 0.06 | 0 | 0.01 | 0.03 | 0.06 |
| $FeCl_2$ | D7 | 21.64 | 25.14 | 14.61 | 0 | 57.89 | 32.14 | 11.1 | 30.81 |
| | D9 | 28.12 | 16.56 | 6.48 | 12.36 | 86.23 | 33.63 | 10.98 | 6.38 |
| $FeCl_3$ | D7 | 21.64 | 30.4 | 24.32 | 0 | 57.89 | 82.84 | 54.5 | 15.01 |
| | D9 | 28.12 | 29.31 | 11.02 | 15.98 | 86.23 | 75.41 | 40.89 | 15.66 |
| $FeSO_4$ | D7 | 21.64 | 31.21 | 3.45 | 32.12 | 57.89 | 47.03 | 7.62 | 23.01 |
| | D9 | 28.12 | 20.63 | 0 | 18.23 | 86.23 | 38.07 | 6.77 | 10.83 |
| $CuCl_2$ | D7 | 21.64 | 3.24 | 0 | 0 | 57.89 | 11.69 | 17.88 | 0 |
| | D9 | 28.12 | 3.23 | 0 | 0 | 86.23 | 10.93 | 18.58 | 9.45 |
| $CuSO_4$ | D7 | 21.64 | 7.28 | 0 | 0 | 57.89 | 42.34 | 10.23 | 0 |
| | D9 | 28.12 | 7.81 | 0 | 0 | 86.23 | 30.57 | 8.09 | 8.06 |
| $CoCl_2$ | D7 | 21.64 | 0 | 0 | 0 | 57.89 | 33.69 | 27.41 | 30.63 |
| | D9 | 28.12 | 0 | 0 | 2.68 | 86.23 | 40.12 | 33.18 | 29.56 |
| $CoSO_4$ | D7 | 21.64 | 0 | 0 | 0 | 57.89 | 55.75 | 71.22 | 16.72 |
| | D9 | 28.12 | 0 | 0 | 6.66 | 86.23 | 39.73 | 40.23 | 29.07 |
| $MnCl_2$ | D7 | 21.64 | 28.12 | 51.55 | 19.76 | 57.89 | 60.37 | 101.26 | 21.41 |
| | D9 | 28.12 | 32.23 | 50.57 | 7.51 | 86.23 | 88.01 | 131.2 | 9.25 |
| $ZnSO_4$ | D7 | 21.64 | 28.6 | 28.01 | 36.66 | 57.89 | 115.54 | 104.97 | 54.48 |
| | D9 | 28.12 | 28.59 | 20.14 | 23.57 | 86.23 | 113.53 | 106.29 | 39.42 |

Example 7

Effect on a Biocatalytic Reaction of pH Adjustment

As the biocatalytic reaction proceeds, pH of a reaction solution is continuously increased. In a case where a fixed pH of a reaction solution was maintained, in order to test an effect on the biocatalytic reaction, the biocatalytic reaction was carried out by using a 5 L fermentation tank. The culture condition was the same as that in Example 1 except that 140 ml liquid culture solution was used for an intermediate culture, and 3.5 L liquid medium was used for a main culture. The reaction condition was based on that in Examples 1 to 6.

After the completion of the main culture of ID9302 for 5 days, ID9302 GAC as a biocatalyst was prepared. In a 5 L fermentation tank as a reaction tank, 3.5 L of a TSSMC buffer (pH 7.2) including 0.03% $MnCl_2$ was placed, and ID9302 GAC was re-dissolved in the reaction buffer. Then, the reaction system was maintained in equilibrium with 28° C., 500 rpm, and 0.5 vvm. Vitamin D3 and β-cyclodextrin, corresponding to 0.02% and 0.05% with respect to 3.5 L reaction solution, were dissolved in 52.5 ml of methanol, and then continuously administered for 5 days from the start of the reaction. Herein, a pH was maintained at 6.2, 6.6, 7.0, 7.4, 7.8, and 8.0 by using 1N NaOH and 0.5N HCl. The $6^{th}$, $8^{th}$, and $10^{th}$ day reaction solutions of the biocatalyst were subjected to HPLC analysis in the same manner as that of Example 1-2, and then the productivity of calcifediol and calcitriol was tested.

Figure 7:
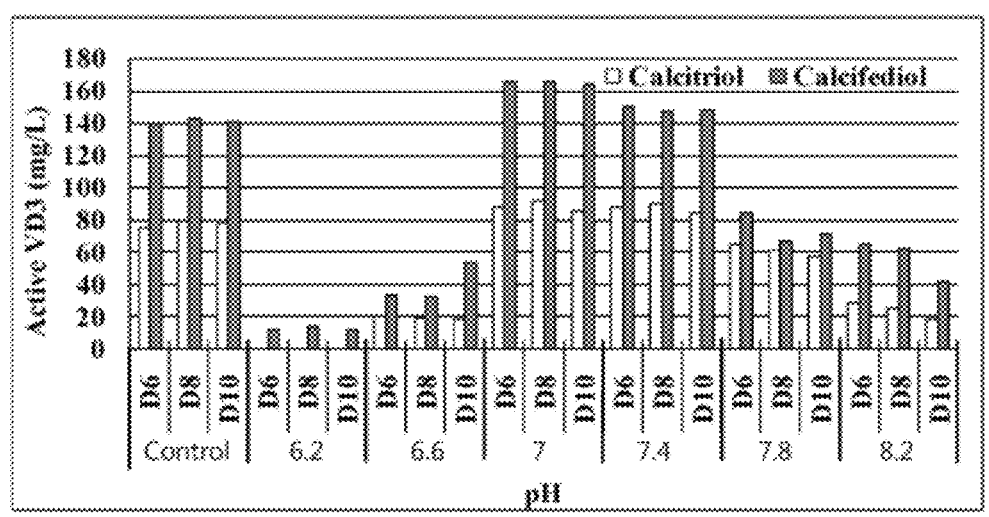
FIG. 7 is a graph showing that calcifediol and calcitriol are produced when a predetermined pH is maintained during a biocatalytic reaction (number d: a period (days) from the start of the reaction)

As a result, at pH 6.2, bioconversion was not carried out at all, and thus calcitriol and calcifediol were hardly produced. Also, at pH 6.6, the production yields of calcitriol and calcifediol were very low. Meanwhile, at pH 7, and 7.4, the production yields of calcitriol and calcifediol were high. At pH 7.0, the productivities of calcitriol and calcifediol were increased 1.15 times and 1.16 times, compared to those of a control group. At pH 7.4, the productivities were increased 1.12 times and 1.03 times. At pH 7.8 and 8.2, the production yields of calcitriol and calcifediol were suddenly decreased (see FIG. 7 and Table 6).

As can be seen from the result, the maintenance of a predetermined pH during a biocatalytic reaction can increase the production yields of calcifediol and calcitriol. Herein, it is preferable to maintain a pH within a range of 7.0 to 7.4.

TABLE 6

Effect on a biocatalytic reaction of pH adjustment

| pH | Reaction time | Amount of produced calcitriol (mg/L) | Amount of produced calcifediol (mg/L) |
|---|---|---|---|
| Control group | D6 | 75.32 | 140.23 |
| | D8 | 80.23 | 142.54 |
| | D10 | 78.34 | 141.33 |
| 6.2 | D6 | 0 | 12.53 |
| | D8 | 0 | 14.65 |
| | D10 | 0 | 12.32 |
| 6.6 | D6 | 20.51 | 33.57 |
| | D8 | 19.71 | 32.75 |
| | D10 | 18.36 | 53.43 |
| 7.0 | D6 | 88.4 | 165.87 |
| | D8 | 91.96 | 166.05 |
| | D10 | 85.14 | 163.84 |
| 7.4 | D6 | 87.88 | 150.61 |
| | D8 | 89.98 | 147.23 |
| | D10 | 83.97 | 148.08 |
| 7.8 | D6 | 64.75 | 84.04 |
| | D8 | 61.32 | 67.245 |
| | D10 | 57.11 | 71.791 |
| 8.2 | D6 | 28.63 | 64.74 |
| | D8 | 25.06 | 62.13 |
| | D10 | 18.99 | 41.4 |

Example 8

Comparison of Productivity Between Calcifediol and Calcitriol According to Kinds of Metallic Compounds in a 75 L Fermentation Tank Based on the reaction condition obtained from Examples 1 to 7, a production test of calcifediol and calcitriol was carried out in which a hydroxylic group was introduced to vitamin D3 by using a biocatalyst in a 75 L fermentation tank. The culture condition was the same as that in Example 1 except that through scale-up, 2 L liquid culture solution was used for an intermediate culture, and 50 L liquid medium (in a 75 L fermentation tank) was used for a main culture.

After the completion of the main culture of ID9302 for 5 days, ID9302 GAC as a biocatalyst was prepared. In a 75 L fermentation tank as a reaction tank, 50 L of a TSSM buffer was placed, and 9 kinds of metallic compounds noted in Table 5 were administered in such a manner that concentrations can be 0.01%, 0.03%, and 0.06%.

GAC was re-dissolved in the reaction buffer. Then, the reaction system was maintained in equilibrium with 28° C., 500 rpm, and 0.5 vvm. Vitamin D3 and β-cyclodextrin, corresponding to 0.02% and 0.05% with respect to 50 L reaction solution, were dissolved in 750 ml of methanol, and then continuously administered for 5 days from the start of the reaction.

Herein, a pH was maintained at 7.0 by using 1N NaOH and 0.5N HCl. For 10 days, reaction solutions of the biocatalyst were subjected to HPLC analysis in the same manner as that of Example 1-2, and then the productivity of calcifediol and calcitriol was tested.

Figure 8:
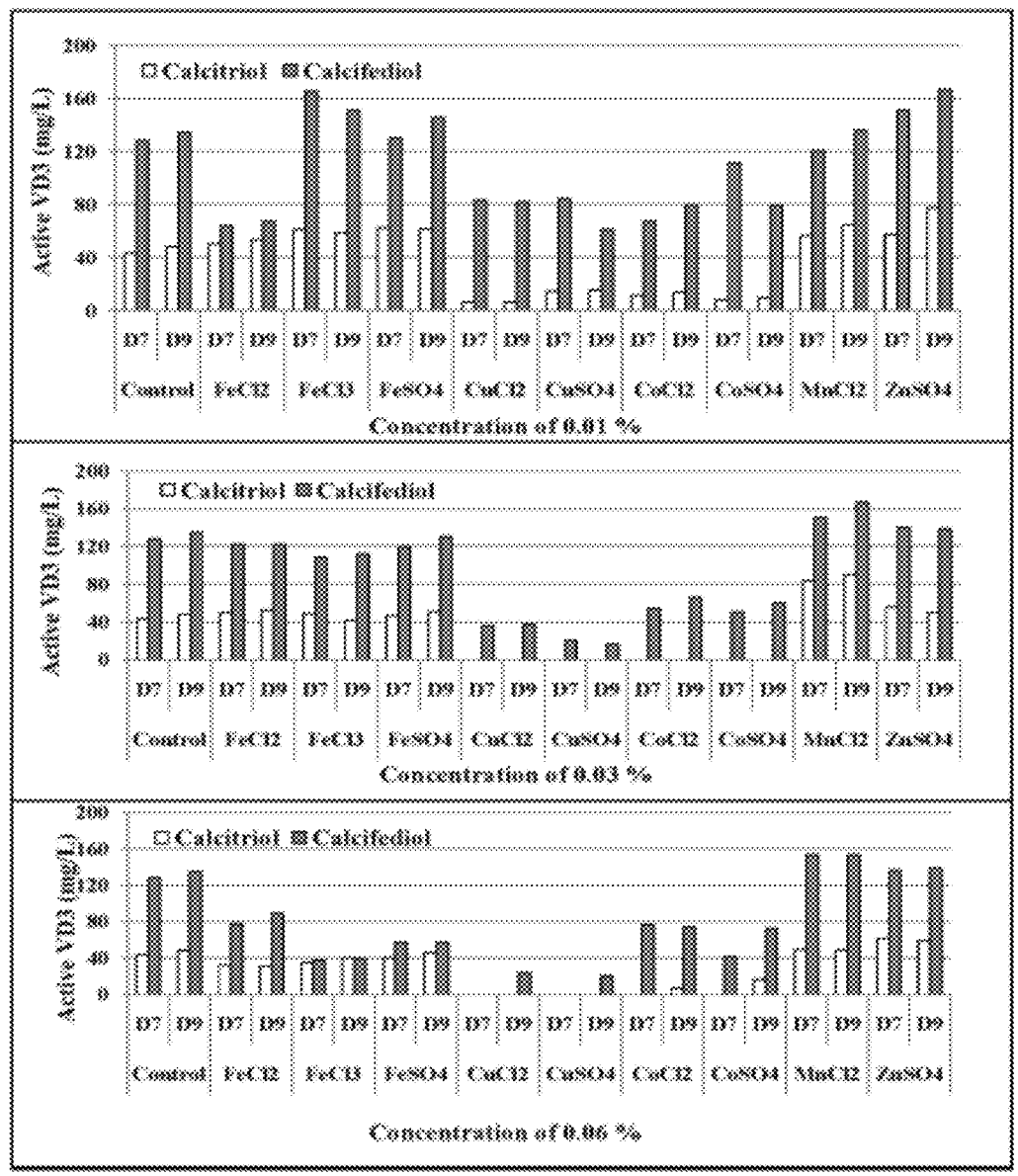
FIG. 8 is a graph showing that calcifediol and calcitriol are produced, in which a metallic compound has an effect on a biocatalytic reaction in a 75 l fermentation tank while bio-converting vitamin D3 (number d: a period (days) from the start of the reaction)

As a result, as noted in Table 7, when $CuCl_2$, $CuSO_4$, $CoCl_2$, and $CoSO_4$ were used, the biocatalytic reaction was not sufficiently performed irrespective of concentrations. Meanwhile, $FeCl_2$, $FeCl_3$, and $FeSO_4$, at a concentration of 0.01%, showed calcitriol production yields of 53.12 mg/L, 60.8 mg/L, and 62.42 mg/L, respectively. Also, $ZnSO_4$, at a concentration of 0.01%, showed a calcitriol production yield of 77.18 mg/L. Especially, $MnCl_2$, at a concentration of 0.03%, showed a calcitriol production yield of 90.12 mg/L and a calcifediol production yield of 166.87 mg/L (see FIG. 8).

Accordingly, it can be seen that the inventive composition including $FeCl_2$, $FeCl_3$, $FeSO_4$, $ZnSO_4$ and $MnCl_2$ showed a high calcitriol or calcifediol productivity.

Example 9

Comparison of Productivity Between Calcifediol and Calcitriol According to Kinds of Organic Solvents in a 75 L Fermentation Tank Based on the reaction condition obtained from Examples 1 to 7, a production test of calcifediol and calcitriol was carried out in which a hydroxylic group was introduced to vitamin D3 by using a biocatalyst in a 75 L fermentation tank.

The culture condition was the same as that in Example 8. After the completion of the main culture of ID9302 for 5 days, ID9302 GAC as a biocatalyst was prepared. In a 75 L fermentation tank as a reaction tank, 50 l of a TSSMC buffer including 0.03% $MnCl_2$ at a final concentration was placed, and then ethanol, methanol, acetone, and DMSO were administered at respective concentrations showing the highest productivity in Example 4.

GAC was re-dissolved in the reaction buffer. 300 ml of 10% vitamin D3 solution was prepared and introduced to a biocatalytic reaction system in equilibrium. Then, bioconversion of vitamin D3 was carried out under the condition of 28° C., 500 rpm, and 0.5 vvm for 10 days.

Herein, a pH was maintained at 7.0 by using 1N NaOH and 0.5N HCl. For 10 days, reaction solutions of the biocatalyst were subjected to HPLC analysis in the same manner as that of Example 1-2, and then the productivity of calcifediol and calcitriol was tested.

As a result, as noted in Table 8, ethanol showed a calcitriol production yield of 48.45 mg/L, and acetone and DMSO showed calcitriol production yields of 74.87 mg/L and 70.85 mg/L, respectively, and calcifediol production yields of 156.37 mg/L and 141.81 mg/L, respectively. Especially, methanol showed a calcitriol production yield of 90.12 mg/L, and a calcifediol production yield of 166.87 mg/L.

Accordingly, it can be seen that the inventive composition including methanol, ethanol, acetone, and DMSO showed a high calcitriol or calcifediol productivity.

TABLE 7

Change in amounts of produced calcitriol and calcifediol according to the kinds of metallic compounds

| Metallic compound | Reaction time | Amount of produced calcitriol (mg/l) concentration (%) | | | | Amount of produced calcifediol (mg/l) concentration (%) | | | |
|---|---|---|---|---|---|---|---|---|---|
| | | 0 | 0.01 | 0.03 | 0.06 | 0 | 0.01 | 0.03 | 0.06 |
| $FeCl_2$ | D7 | 43.27 | 50.28 | 50.22 | 32.17 | 128.18 | 64.28 | 122.21 | 77.02 |
| | D9 | 48.39 | 53.12 | 52.96 | 30.94 | 134.76 | 67.26 | 121.96 | 89.13 |
| $FeCl_3$ | D7 | 43.27 | 60.8 | 48.64 | 35.18 | 128.18 | 165.68 | 109.03 | 37.52 |
| | D9 | 48.39 | 58.62 | 42.04 | 39.95 | 134.76 | 150.82 | 111.78 | 39.15 |
| $FeSO_4$ | D7 | 43.27 | 62.42 | 46.9 | 40.35 | 128.18 | 130.15 | 120.24 | 57.52 |
| | D9 | 48.39 | 61.26 | 50.84 | 45.57 | 134.76 | 146.14 | 130.54 | 57.07 |
| $CuCl_2$ | D7 | 43.27 | 6.48 | 0 | 0 | 128.18 | 83.38 | 35.76 | 0 |
| | D9 | 48.39 | 6.46 | 0 | 0 | 134.76 | 81.86 | 37.16 | 23.62 |
| $CuSO_4$ | D7 | 43.27 | 14.56 | 0 | 0 | 128.18 | 84.68 | 20.46 | 0 |
| | D9 | 48.39 | 15.62 | 0 | 0 | 134.76 | 61.14 | 16.18 | 20.15 |
| $CoCl_2$ | D7 | 43.27 | 11.23 | 0 | 0 | 128.18 | 67.38 | 54.82 | 76.57 |
| | D9 | 48.39 | 13.84 | 0 | 6.7 | 134.76 | 80.24 | 66.36 | 73.9 |
| $CoSO_4$ | D7 | 43.27 | 8.37 | 0 | 0 | 128.18 | 111.5 | 50.44 | 41.8 |
| | D9 | 48.39 | 9.79 | 0 | 16.65 | 134.76 | 79.46 | 60.46 | 72.67 |
| $MnCl_2$ | D7 | 43.27 | 56.24 | 83.1 | 49.4 | 128.18 | 120.74 | 150.12 | 153.52 |
| | D9 | 48.39 | 64.46 | 90.12 | 48.77 | 134.76 | 136.02 | 166.87 | 153.21 |
| $ZnSO_4$ | D7 | 43.27 | 57.2 | 56.02 | 61.65 | 128.18 | 151.08 | 140.25 | 136.2 |
| | D9 | 48.39 | 77.18 | 50.28 | 58.92 | 134.76 | 167.06 | 138.67 | 138.55 |

TABLE 8

Change in amounts of produced calcitriol and
calcifediol according to the kinds of organic solvents

| Organic solvent | Reaction time | Amount of produced calcitriol (mg/l) | Amount of produced calcifediol (mg/l) |
|---|---|---|---|
| ethanol (5%) | D7 | 33.24 | 113.01 |
|  | D9 | 48.45 | 128.96 |
| methanol (7.5%) | D7 | 83.10 | 150.12 |
|  | D9 | 90.12 | 166.87 |
| Acetone (10%) | D7 | 63.12 | 148.28 |
|  | D9 | 74.87 | 156.37 |
| DMSO (5%) | D7 | 62.32 | 131.87 |
|  | D9 | 70.85 | 141.81 |

Example 10

Production of Calcifediol (Activated Vitamin D3) and Calcitriol Through a Biocatalytic Reaction in a 75 L Fermentation Tank Based on the reaction conditions determined from Examples 1 to 9, a calcifediol/calcitriol production test was carried out in which a hydroxylic group was introduced to vitamin D3 by using a biocatalyst in a 75 L fermentation tank. The culture condition was the same as that in Example 9.

After the completion of the main culture of ID9302 for 5 days, ID9302 GAC as a biocatalyst was prepared. In a 75 L fermentation tank as a reaction tank, 50 L of a TSSMM buffer was placed, and GAC was re-dissolved in the reaction buffer. Then, the reaction system was maintained in equilibrium with 28° C., 500 rpm, and 0.5 vvm. Vitamin D3 and β-cyclodextrin, corresponding to 0.02% and 0.05% with respect to 50 L reaction solution, were dissolved in 750 ml of methanol, and then continuously administered for 5 days from the start of the reaction. Herein, a pH was maintained at 7.0 by using 1N NaOH and 0.5N HCl. For 10 days, reaction solutions of the biocatalyst were subjected to HPLC analysis in the same manner as that of Example 1-2, and then the productivity of calcifediol and calcitriol was tested.

Figure 9:
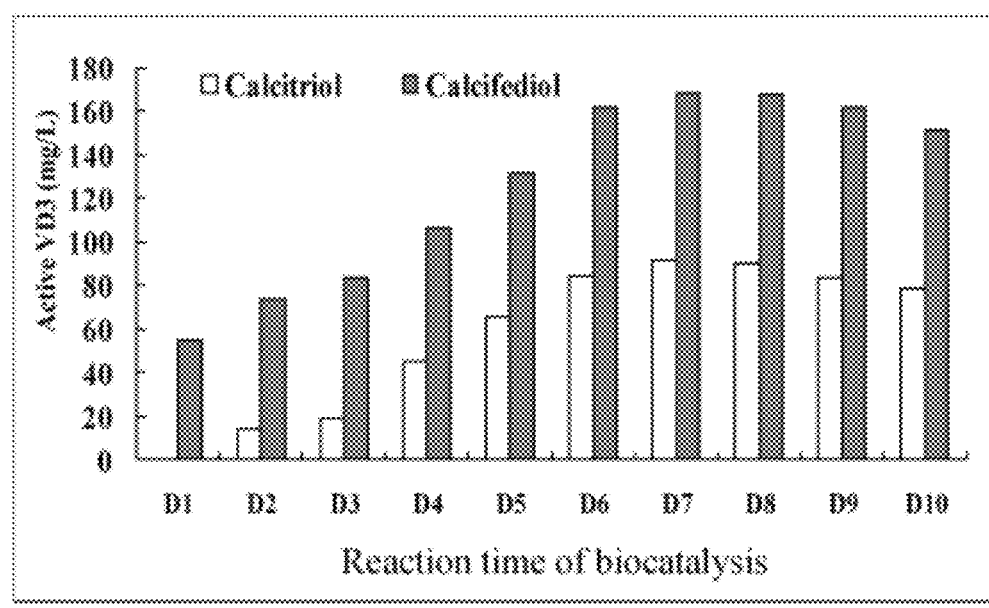
FIG. 9 is a graph showing that calcifediol (activated vitamin D3) and calcitriol are produced from vitamin D3 through a biocatalytic reaction in a 75 l fermentation tank (number d: a period (days) from the start of the reaction).

As a result, on the $1^{st}$ day of a biocatalytic reaction, the production of calcifediol as a precursor of calcitriol was started. Then, on the $2^{nd}$ to $3^{rd}$ day of the reaction, production of calcifediol was suddenly increased, and at the same time, the production of calcitriol was in actuality started. On the $4^{th}$ day of the biocatalytic reaction, the production of calcitriol and calcifediol was suddenly increased, and on the $7^{th}$ day of the biocatalytic reaction, the productivity of calcitriol was the highest (91.23 mg/L), and the productivity of calcifediol was 168.24 mg/L. Compared to that on the $1^{st}$ day of reaction, the productivity of calcitriol was increased 90 times, and the productivity of calcifediol was increased 3 times. On the $10^{th}$ day of the biocatalytic reaction from the maximum production, the productivities of the two materials were slowly decreased (see FIG. 9).

Accordingly, it can be found that when a biocatalyst was prepared by ID9302 and the reaction was carried out in a 75 L fermentation tank, it is possible to introduce a hydroxylic group to vitamin D3 and at the same time to achieve a high productivity of calcitriol and calcifediol.

Furthermore, besides the method according to the present invention, it can be found that an increase in the amount of a substrate within a concentration range causing no reduction in biocatalyst enzyme activity can increase the productivity of calcitriol or calcifediol as a final product.

Example 11

Separation of Activated Vitamin D3 from a Reaction Solution

After the biocatalytic reaction, 50 L of a reaction solution was added with 1% synthetic absorbent, Sepabeads SP850 (Mitsubishi chemical, Japan). Then, through a stirring process at 400rpm for 1 hour, vitamin D3 and activated vitamin D3 within the reaction solution were absorbed. Cells and SP850, filtered by a multi-layer filtering apparatus, were extracted with 25 L of acetone, and vacuum-concentrated at 40° C. or less.

The concentrate was re-dissolved in 2 L of 50% methanol, and added with 2 L hexane through a separatory funnel, followed by first re-extraction. The extract (upper phase, calcifediol in hexane, vitamin D3, fat-soluble impurities) was collected. The extract was vacuum-concentrated at 40° C. or less, and collected by silica gel column (moving phase: a 7:3 hexane/ethyl acetate mixture, and flow rate: 10 ml/min). Vitamin D3 and calcifediol were sequentially collected. Vitamin D3 and calcifediol had a purity of 90% or more, and were collected in amounts of 18 g and 7.6 g, respectively. They were capable of being re-used as a precursor for producing calcitriol.

The residue from the first re-extraction (lower phase, calcitriol in 50% methanol, soluble impurities) was secondly re-extracted with 2 L dichloromethane, so as to collect a calcitriol extract with no soluble impurities (lower phase, calcitriol in dichloromethane). The extract was vacuum-concentrated at 40° C. or less, and calcitriol was separately collected by C-18 ODS column (moving phase: 75% methanol, and flow rate: 10 ml/min). The collected calcitriol was vacuum-concentrated at 40° C. or less, and then dissolved in methanol so as to separate αtype calcitriol from βtype calcitriol through YMC J'sphere ODS column. Through the separation was carried out under a condition of moving phase of 45% acetonitrile, 230 nm, 15 ml/min so as to provide 2.2 g of white crystalline calcitriol with a purity of 99%.

As can be seen from the foregoing, the present invention provides a buffer composition promoting calcitriol or calcifediol production, and a method for producing calcitriol or calcifediol using the same. In the inventive production method, the production yield of calcitriol or calcifediol is high, and the bioconversion is carried out in a catalytic reaction system instead of in a microorganism culture system. Thus, it is not required to maintain a sterile state. Also, the separation/purification following the completion of a biocatalytic reaction can be carried out in a cleaner state than the microorganism culture method. Accordingly, there is an advantage in that a cost required for separation is low and the quality is improved. Furthermore, the inventive calcitriol or calcifediol production promoting buffer composition can provide a high productivity of calcitriol or calcifediol.

The invention claimed is:
1. A buffer composition for promoting production of calcitriol or calcifediol by biocatalytic reaction of growth-arrested cells of *Pseudonocardia autotrophica*, the buffer composition consisting of 0.01 to 0.3% (w/v) at least one metallic compound selected from the group consisting of $FeCl_2$, $FeCl_3$, $FeSO_4$, $MnCl_2$, and $ZnSO_4$, 1 to 10% (w/v) of at least one organic solvent selected from the group consisting of ethanol, methanol, acetone, and dimethyl sulfoxide (DMSO), 0.1 to 5% (w/v) of cyclodextrin, 0.01 to 1% (w/v) of tris (hydroxymethyl)aminomethane, 0.01 to 1% (w/v) of sodium succinate, 0.01 to 1% (w/v) of sodium chloride, 0.001 to 0.5% (w/v) of magnesium chloride, and a residual quantity of water.

2. The buffer composition for promoting production of calcitriol or calcifediol of claim 1, wherein the metallic compound is in a concentration of 0.01 to 0.03% (w/v), the organic solvent is in a concentration of 2.5 to 10% (w/v), the cyclodextrin is in a concentration of 0.25 to 1% (w/v), the tris(hydroxymethyl)aminomethane is in a concentration of 0.12 to 0.61% (w/v), the sodium succinate is in a concentration of 0.16 to 0.8% (w/v), the sodium chloride is in a concentration of 0.06 to 0.18% (w/v) and the magnesium chloride is in a concentration of 0.006 to 0.05% (w/v) of the composition.

3. The buffer composition for promoting production of calcitriol or calcifediol of claim 1, wherein the metallic compound is $MnCl_2$.

4. The buffer composition for promoting production of calcitriol or calcifediol of claim 1, wherein the organic solvent is methanol.

5. The buffer composition for promoting production of calcitriol or calcifediol of claim 1, wherein the cyclodextrin is β-cyclodextrin.

6. A method for producing calcitriol or calcifediol, comprising the steps of;
   (a) culturing *Pseudonocardia autotrophica*;
   (b) collecting microbial cells from the culture solution; and
   (c) mixing the collected microbial cells, vitamin D3, and the buffer composition for promoting production of calcitriol or calcifediol of anyone of claims 1 to 5.

7. The method for producing calcitriol or calcifediol of claim 6, wherein the *Pseudonocardia autotrophica* is *Pseudonocardia autotrophica* ID9302.

* * * * *